United States Patent
Katra et al.

(10) Patent No.: US 10,335,053 B2
(45) Date of Patent: *Jul. 2, 2019

(54) SYSTEM AND METHOD FOR CARDIAC MONITORING USING ADAPTIVE SENSITIVITY/SPECIFICITY LEVELS

(71) Applicant: Medtronic Monitoring, Inc., San Jose, CA (US)

(72) Inventors: Rodolphe Katra, Blaine, MN (US); Niranjan Chakravarthy, Eden Prairie, MN (US)

(73) Assignee: Medtronic Monitoring, Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/196,730

(22) Filed: Nov. 20, 2018

(65) Prior Publication Data

US 2019/0082989 A1    Mar. 21, 2019

Related U.S. Application Data

(63) Continuation of application No. 15/278,644, filed on Sep. 28, 2016, now Pat. No. 10,159,423.

(51) Int. Cl.
    *A61B 5/04*     (2006.01)
    *A61B 5/0464*   (2006.01)
    (Continued)

(52) U.S. Cl.
    CPC .......... *A61B 5/0464* (2013.01); *A61B 5/0022* (2013.01); *A61B 5/0031* (2013.01);
    (Continued)

(58) Field of Classification Search
    CPC . A61B 5/0464; A61B 5/04012; A61B 5/7264; A61B 5/0022; A61B 5/0031;
    (Continued)

(56) References Cited

U.S. PATENT DOCUMENTS 4,830,006 A   5/1989   Haluska et al.
4,940,054 A   7/1990   Grevis
              (Continued)

FOREIGN PATENT DOCUMENTS

EP   1114653 A2   7/2001
EP   2777494 A1   9/2014
                (Continued)

OTHER PUBLICATIONS

International Search Report and Written Opinion for PCT/US2017/053635 dated Jan. 24, 2018, 15 pages.
(Continued)

*Primary Examiner* — Christopher Koharski
*Assistant Examiner* — Roland Dinga
(74) *Attorney, Agent, or Firm* — Billion & Armitage; Michael A. Collins

(57) ABSTRACT

Embodiments of the present disclosure describe methods of adaptive arrhythmia detection comprising monitoring ECG signals of a patient via a patient medical device, detecting and capturing ECG segments based on a heart rate threshold and an initial sensitivity level associated with the heart rate threshold; and adjusting the sensitivity level based on previously captured ECG segments. Embodiments of the present disclosure further describe patient medical devices comprising one or more electrodes and sensing circuitry for monitoring ECG signals of a patient; and a processing module configured to receive the monitored ECG signal, wherein the processing module detects and captures ECG segments based on a plurality of heart rate thresholds and one or more sensitivity levels associated with each of the heart rate thresholds, and adjusts at least one of the one or more sensitivity levels associated with each of the heart rate thresholds.

19 Claims, 5 Drawing Sheets

(51) Int. Cl.
*A61B 5/00* (2006.01)
*G06F 19/00* (2018.01)

(52) U.S. Cl.
CPC .......... *A61B 5/04012* (2013.01); *A61B 5/686* (2013.01); *A61B 5/7225* (2013.01); *A61B 5/7264* (2013.01); *A61B 5/7275* (2013.01); *G06F 19/00* (2013.01); *A61B 5/6867* (2013.01); *A61B 2505/07* (2013.01); *A61B 2560/0468* (2013.01); *A61B 2560/0481* (2013.01)

(58) Field of Classification Search
CPC ..... A61B 5/7275; A61B 5/7225; A61B 5/686; A61B 5/6867; A61B 2560/0481; A61B 2560/0468; A61B 2505/07; G06F 19/00
See application file for complete search history.

(56) References Cited

U.S. PATENT DOCUMENTS

| | | | |
|---|---|---|---|
| 5,607,460 A | 3/1997 | Kroll et al. | |
| 6,625,490 B1 | 9/2003 | McClure | |
| 6,650,931 B1 | 11/2003 | McClure | |
| 6,922,584 B2 | 7/2005 | Wang et al. | |
| 7,031,765 B2 | 4/2006 | Ritcher et al. | |
| 7,280,869 B2 | 10/2007 | Warman et al. | |
| 7,447,544 B1 | 11/2008 | Kroll | |
| 7,634,310 B2 | 12/2009 | Lee et al. | |
| 8,175,708 B1 | 5/2012 | Snell et al. | |
| 8,326,407 B2 | 12/2012 | Linker | |
| 8,694,098 B2 | 4/2014 | Vincent et al. | |
| 8,790,259 B2 | 7/2014 | Katra et al. | |
| 8,897,863 B2 | 11/2014 | Linker | |
| 8,965,498 B2 | 2/2015 | Katra et al. | |
| 9,173,615 B2 | 11/2015 | Katra et al. | |
| 9,314,178 B2 | 4/2016 | Katra et al. | |
| 10,159,423 B2 * | 12/2018 | Katra .................. | A61B 5/0464 |
| 2007/0213599 A1 | 9/2007 | Siejko et al. | |
| 2008/0051843 A1 | 2/2008 | Li et al. | |
| 2009/0287268 A1 | 11/2009 | Nabutovsky et al. | |
| 2011/0257535 A1 | 10/2011 | Michelson et al. | |
| 2012/0101392 A1 | 4/2012 | Bhunia et al. | |
| 2013/0274584 A1 | 10/2013 | Finlay et al. | |
| 2014/0371604 A1 | 12/2014 | Katra et al. | |
| 2015/0088216 A1 | 3/2015 | Gordon et al. | |
| 2015/0126822 A1 | 5/2015 | Chavan et al. | |
| 2016/0045131 A1 | 2/2016 | Siejko | |
| 2016/0135708 A1 | 5/2016 | Chakravarthy et al. | |

FOREIGN PATENT DOCUMENTS

| | | |
|---|---|---|
| WO | 2015066430 A1 | 5/2015 |
| WO | 2016007657 A1 | 1/2016 |

OTHER PUBLICATIONS

International Search Report and Written Opinion for PCT/US2017/053651 dated Dec. 4, 2017, 13 pages.
"Tachycardia With a Pulse Algorithm", ACLS Training Center 1998, 1 page.
Garcia, et al., "Arrhythmia Recognition, the Art of Interpretation", Jones & Bartlett Learning, First Edition, Nov. 12, 2003, 392-393, 534-535.

* cited by examiner

SYSTEM AND METHOD FOR CARDIAC MONITORING USING ADAPTIVE SENSITIVITY/SPECIFICITY LEVELS

TECHNICAL FIELD

The present disclosure is related in general to patient monitoring and in particular to detecting cardiac rhythm disorders.

BACKGROUND

Cardiac monitoring—particularly ambulatory monitoring—includes long-term monitoring of ECG signals to detect various type of heart rhythm disorders. The amount of ECG data collected, however, precludes (or makes cost-prohibitive) health care professional (HCP) review of the data. Automatic processing of the collected ECG data is utilized to detect and capture ECG segments corresponding with detected heart rhythm disorders. However, while some of the ECG segments captured correspond with an actual heart rhythm disorder (i.e., a true positive event), other ECG segments are incorrectly identified as corresponding to a heart rhythm disorder (i.e., a false positive event). On the other hand, capturing multiple ECG segments corresponding with the same heart rate rhythm disorder is not always diagnostically relevant. For instance, the first tachy150 event captured is diagnostically relevant, but the other tachy150 events captured on the same day may not be. In addition, each captured ECG segment identified as corresponding to a heart rhythm disorder and captured represents a cost. That cost includes the cost of storing the captured ECG segment either on the monitoring device or externally, the cost of power required to communicate the captured ECG segment from the monitoring device to a remote monitoring center, and/or time required for a HCP to review the captured ECG episode and determine whether action is required. Thus, it is beneficial to reduce the ECG segments incorrectly identified as corresponding to a heart rhythm disorder (i.e., minimize false positive events). However, it is also important to ensure that heart rhythm disorders are detected and corresponding ECG segments captured and provided to a human HCP for review (i.e., avoid missing detection of positive events, or false negative).

It would therefore be beneficial to provide a monitoring system that balances these concerns to ensure clinically relevant ECG segments are captured while maintaining a low-cost system.

SUMMARY

In general, embodiments of the present disclosure describe methods and systems of adaptive arrhythmia detection.

Accordingly, embodiments of the present disclosure describe a method of adaptive arrhythmia detection, the method comprising monitoring arrhythmic ECG signals of a patient via a patient monitoring device, detecting arrhythmic ECG signals based on a threshold heart rate, capturing an arrhythmic ECG episode based on a sensitivity profile associated with the threshold heart rate, and modifying the sensitivity of the sensitivity profile.

Embodiments of the present disclosure further describe methods of adaptive arrhythmia detection, the method comprising monitoring arrhythmic ECG signals of a patient via a patient monitoring device, detecting arrhythmic ECG signals for a plurality of threshold heart rates, capturing an arrhythmic ECG episode based on a sensitivity profile associated with each of the plurality of threshold heart rates, and modifying the sensitivity of at least one of the sensitivity profiles.

Embodiments of the present disclosure also describe a patient monitoring system, the system comprising one or more electrodes and sensing circuitry for monitoring arrhythmic ECG signals of a patient, and a processing module configured to receive the monitored ECG signal, wherein the processing module detects arrhythmic ECG signals for a plurality of threshold heart rates, captures an arrhythmic ECG episode based on a sensitivity profile associated with each of the plurality of threshold heart rates, and modifies the sensitivity of at least one sensitivity profile.

The details of one or more examples are set forth in the description below. Other features, objects, and advantages will be apparent from the description and from the claims.

BRIEF DESCRIPTION OF DRAWINGS

Reference is made to illustrative embodiments that are depicted in the figures, in which.

DETAILED DESCRIPTION

Figure 1:
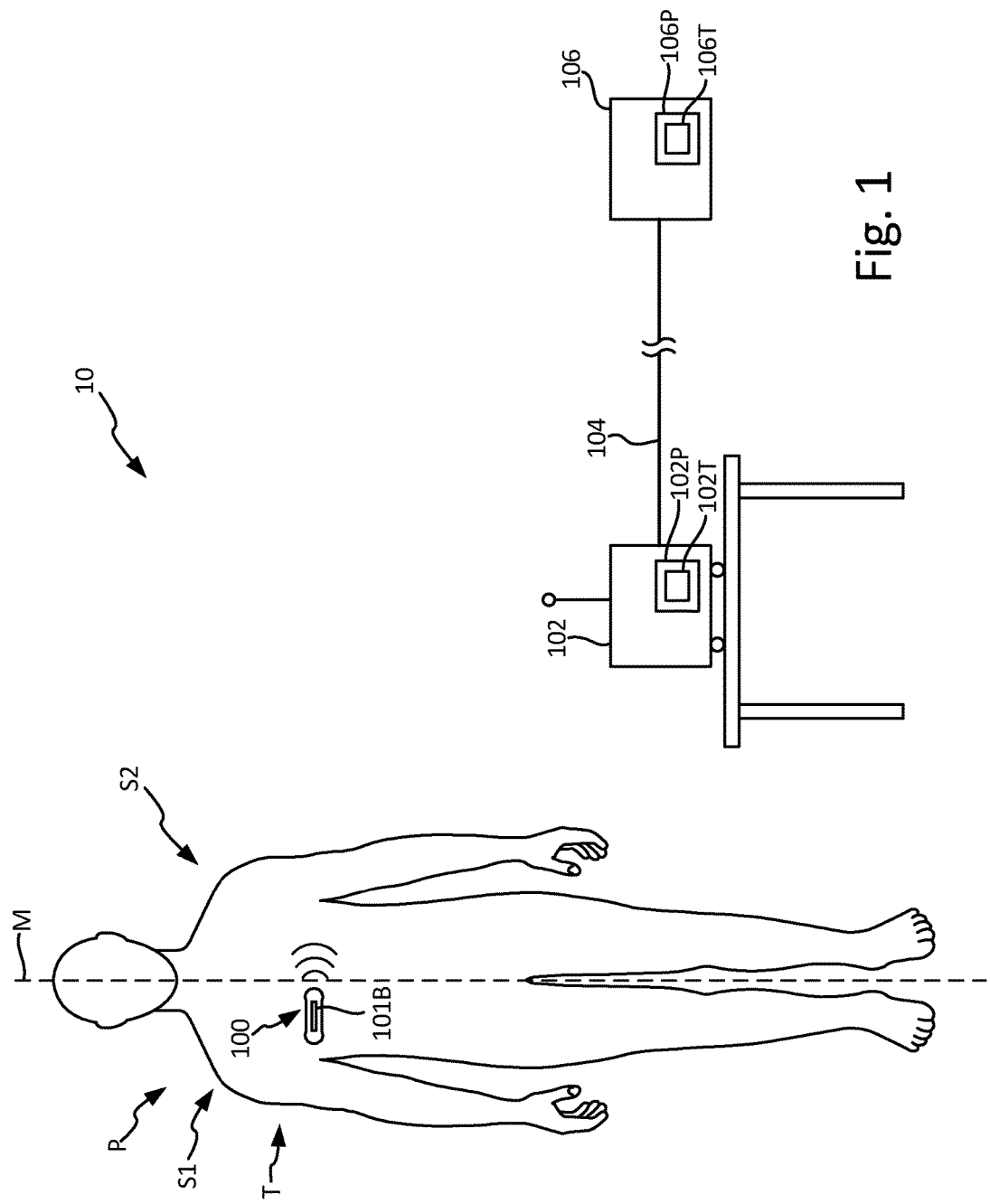
FIG. 1 illustrates a schematic view of a patient and a patient monitoring system, according to one or more embodiments of the present invention.

The present invention relates to patient monitoring devices that use adaptive arrhythmia detection for detecting rate-based arrhythmias, including but not limited to tachycardia and bradycardia. In particular, adaptive arrhythmia detection modifies the detection sensitivity/specificity level associated with various rate-based arrhythmia thresholds in response to a monitored criteria—such as previously detected arrhythmic episode. In this way, the diagnostic yield of captured ECG segments is improved and clinically relevant arrhythmias are reviewed with appropriate priority.

The terms "sensitivity" and "specificity" are used throughout this disclosure. In general, sensitivity is a measure of the proportion of positive events that are correctly identified as such, otherwise referred to as the true positive rate. Specificity is the reciprocal of sensitivity and is a measure of the proportion of negative events that are correctly identified as such, otherwise referred to as the true negative rate. In this way, sensitivity quantifies the avoiding of false negatives while specificity quantifies the avoiding of false positives. Utilizing a higher sensitivity level reduces the risk of missing a true positive event (e.g., arrhythmia), but at a cost of identifying more false positive events (i.e., low specificity, normal sinus rhythm incorrectly identified as arrhythmic) Conversely, utilizing a high specificity reduces the number of false positive events (i.e., ECG segments incorrectly identified as arrhythmic), but at a cost of potentially failing to identify a true positive event (e.g., arrhythmia). Because sensitivity and specificity are reciprocal in nature, most embodiments are described with respect to a rate-based sensitivity level, but it should be understood that a rate-based specificity level may similarly be utilized.

In one embodiment, monitoring devices detect a positive event (e.g., tachycardia, bradycardia, etc.) when the monitored heart rate in X out of the last Y beats (e.g., 13 out of the last 19 beats) exceeds a heart rate threshold (e.g., 130 BPM, 150 BPM, 165 BPM, or 180 BPM). The value of the variables X and Y in this case determine the sensitivity level, and can be modified either alone or in combination to increase or decrease the sensitivity. The sensitivity can be increased by utilizing a smaller ratio of X to Y, and is decreased by increasing the ratio of X to Y. For example, setting X equal to 10 and Y equal to 20 requires that 10 beats out of 20 must exceed the heart rate threshold to trigger capture of the ECG segment. The sensitivity level is increased if X is set equal to 5 and Y remains equal to 20, such that only 5 beats out of 20 must exceed the heart rate threshold to trigger capture of the ECG segment—and is therefore more sensitive. Likewise, the sensitivity level is decreased if X is set equal to 15 and Y is set equal to 18, such that now 15 beats out of 18 must exceed the heart rate threshold to trigger capture of the ECG segment. Specificity may also be defined in terms of the variables X and Y, but whereas sensitivity is increased by lowering the value of the ratio X/Y, specificity is increased by increasing the value of the ratio X/Y. For the sake of simplicity, the present disclosure describes the sensitivity/specificity in terms of level (e.g., high, medium, low) rather than in terms of the value of X/Y utilized to determine the desired sensitivity/specificity level.

FIG. 1 illustrates a patient P and a monitoring system 10 for monitoring cardiac activity, according to one or more embodiments of the present disclosure. Patient P comprises a midline M, a first side S1, for example a right side, and a second side S2, for example a left side. In the embodiment shown in FIG. 1, monitoring system 10 comprises a patient medical device 100, gateway 102, and remote monitoring center 106. In the embodiment shown in FIG. 1, patient medical device 100 is an adherent device that attaches to the skin of the patient, but in other embodiments may be an implantable device, an insertable device, an injectable device, or a wearable device such as a Holter monitor (collectively referred to as a medical device). Exemplary embodiments of suitable medical devices are described in more detail with respect to FIGS. 4, 5, and 6, below. In general, medical device 100 is described herein as providing a monitoring function, but in other embodiments may be configured to provide treatment as well.

Medical device 100 can be adhered/injected/inserted to a patient P at many locations, for example thorax T of patient P. In many embodiments, the device may adhere to one side of the patient, from which side data can be collected. A benefit of utilizing an adherent device, implantable, injectable, or wearable device is that it may be utilized to collect physiological data from the patient while the patient goes about normal day-to-day activities outside of a hospital setting. Medical device 100 may monitor a number of physiological parameters associated with patient P, including electrocardiogram (ECG) signals utilized to detect rhythm abnormalities such as tachycardia and/or bradycardia as well as activity level data, posture, bio-impedance, etc. Analysis of the ECG signals to detect rhythm abnormalities may be done locally by medical device 100 or remotely by gateway 102 and/or remote monitoring center 106 (or similar platform separate from medical device 100). As part of a remote analysis, the reviewer (e.g., prescribing physician) is provided with the sensitivity profiles in order to understand how the device detected and/or captured rate-based arrhythmias. As part of a post-processing analysis (e.g. Holter-type post-processing), the reviewer can remotely adjust sensitivity levels while reviewing the captured data. The reviewer can also adjust sensitivity levels while reviewing the captured data to filter large volumes of captured data.

In embodiments in which the ECG signals are analyzed locally by medical device 100, heart-rate thresholds and rate-dependent sensitivity/specificity levels are utilized to detect rhythm abnormalities such as a tachycardia/bradycardia. In response to a detected rhythm abnormality, medical device 100 captures/stores an ECG segment corresponding to the detected abnormality. In the embodiment shown in FIG. 1, the captured ECG segment is subsequently transmitted to remote monitoring center 106 for review by a health care professional (HCP). Communication of the captured ECG segment may be immediate, or may be delayed for a period of time (i.e., until it is possible/cost effective to communicate the stored ECG segment). In response to the received ECG samples, the HCP may verify the detected rhythm abnormality and take appropriate steps (e.g., prescribe treatment).

In other embodiments in which ECG signals are not analyzed by medical device 100 locally, monitored ECG signals are communicated to an external processor such as gateway 102 or remote monitoring center 106 for analysis and detection of rhythm abnormalities. As discussed above, gateway 102 and/or remote monitoring center 106 similarly utilize heart-rate thresholds and rate-dependent sensitivity/specificity thresholds to detect rhythm abnormalities such as a tachycardia/bradycardia. In response to a detected rhythm abnormality, an ECG segment corresponding with the detected abnormality is captured and stored for subsequent review by a HCP.

In the embodiment shown in FIG. 1, medical device 100 communicates wirelessly with remote center 106. The communication may occur directly (via a cellular or Wi-Fi network), or indirectly through intermediate device or gateway 102. As described above, in one embodiment ECG signals monitored by medical device 100 are communicated in their entirety to remote center 106 for analysis. In other embodiments, medical device 100 processes the monitored ECG signals locally using heart-rate thresholds and rate-dependent sensitivity/specificity thresholds to detect rhythm abnormalities and stores/captures ECG segments corresponding with detected abnormalities.

In one embodiment, gateway 102 comprises components of the zLink™, a small portable device similar to a cell phone that wirelessly transmits information received from medical device 100 to remote monitoring center 106. The gateway 102 may consist of multiple devices, which can communicate wired or wirelessly with remote center 106 in many ways, for example with a connection 104 which may comprise an Internet connection and/or with a cellular connection. Remote center 106 may comprise a hosted application for data analysis and storage that also includes a website, which enables secure access to physiological trends and clinical event information for interpretation and diagnosis. Remote center 106 may further or alternatively comprise a back-end operation where physiological data from adherent device 100 are read by human experts to verify accuracy. Reports may then be generated at remote monitoring center 106 for communication to the patient's physician or care provider. In one embodiment, in addition to one-way communication from medical device 100 to gateway 102 and/or remote monitoring center 106, remote monitoring center 106 may communicate/push heart-rate thresholds and/or rate-dependent sensitivity/specificity thresholds to medical device 100, either to program/initialize medical device 100 or update the values stored by medical device 100.

In an exemplary embodiment, monitoring system 10 comprises a distributed processor system with at least one processing module (not shown) included as part of adherent device 100, at least one processor 102P of gateway 102, and at least one processor 106P at remote center 106, each of which processors can be in electronic communication with the other processors. At least one processor 102P comprises a tangible medium 102T, and at least one processor 106P comprises a tangible medium 106T. Remote processor 106P may comprise a backend server located at the remote center. Physiological parameters—including ECG samples—monitored by medical device 100 may be analyzed by one or more of the distributed processors included as part of medical device 100, gateway 102, and/or remote monitoring center 106.

Figure 2:
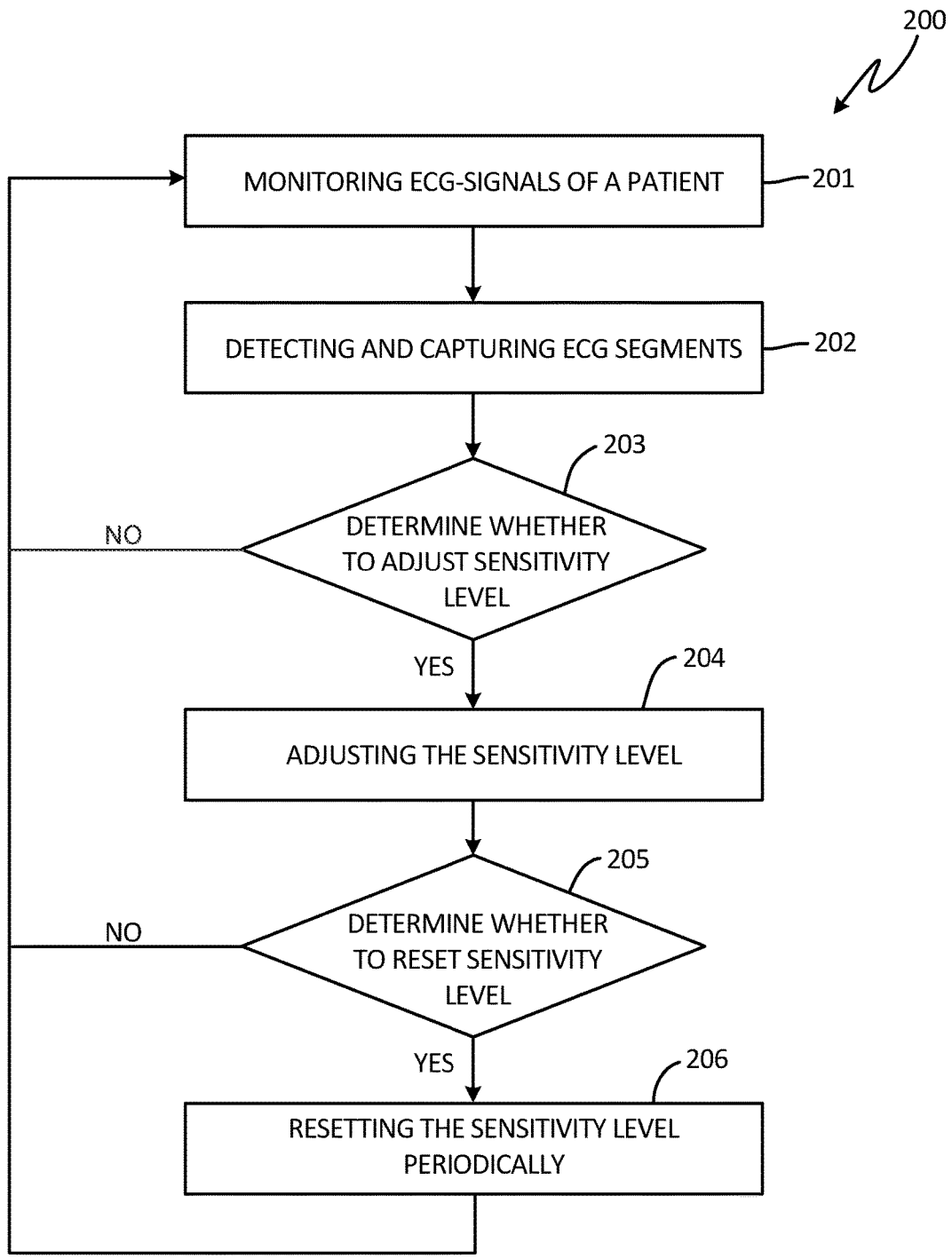
FIG. 2 illustrates a flowchart of a method 200 of adaptively detecting arrhythmias, according to one or more embodiments of the present disclosure.

FIG. 2 illustrates a flowchart of a method 200 of adaptively detecting arrhythmias, according to an embodiment of the present disclosure.

At step 201, ECG signals of a patient are monitored via a patient medical device. As provided in more detail below, monitoring ECG signals can include sensing ECG signals via one or more sensors and circuitry located on the patient medical device. In addition to monitoring ECG signals, other physiological signals can be monitored, including, but not limited to, bioimpedance measurements, respiration measurements, body posture measurements, and activity level measurements.

At step 202, monitored ECG signals are processed to detect and capture abnormal (e.g., arrhythmic) ECG segments based on one or more heart rate thresholds and associated sensitivity/specificity level. In one embodiment, a single sensitivity/specificity level may be utilized for the plurality of heart rate thresholds, but in other embodiments a separate sensitivity/specificity level is associated with each of the plurality of heart-rate thresholds. In the embodiment shown in FIG. 2, arrhythmic ECG segments are detected by counting the number of beats exceeding the defined heart rate threshold. If the number of beats exceeding the heart rate threshold satisfies the sensitivity/specificity level, then the ECG segment corresponding to the detected arrhythmia is captured. For example, as discussed above, the sensitivity/specificity level may require that at least X number of beats out of Y total beats must exceed the defined heart rate threshold in order to trigger capture of an arrhythmic ECG segment.

Detecting and capturing an arrhythmic ECG segment based on one or more heart rate thresholds and an associated sensitivity/specificity level can include one or more of storing the captured arrhythmic ECG segment locally (e.g., on the patient medical device) or remotely (e.g., at a remote monitoring center). Detecting and capturing an arrhythmic ECG segment based on one or more heart rate thresholds and an associated sensitivity/specificity level can also include communicating and/or transmitting the captured arrhythmic ECG segment locally (e.g., communicating to the patient) or remotely (e.g., communicating to a medical professional at a remote monitoring center). Embodiments of the present disclosure can include any combination of storing the captured arrhythmic ECG segment locally and/or remotely and communicating the captured arrhythmic ECG segment locally and/or remotely. In some embodiments, the ECG signal that triggered capture of an ECG segment can be stored and/or communicated for post-monitoring analysis, while the captured ECG segment can be deployed for in-monitoring analysis.

At step 203, a determination is made whether to adjust the sensitivity/specificity level associated with one or more of the heart-rate thresholds. If no adjustment is required, then the method returns to monitoring ECG signals at step 201. If the determination is to adjust the sensitivity level (e.g., yes), the method proceeds to step 204, where the sensitivity level of the sensitivity profile is adjusted.

In some embodiments, the determination of whether to adjust the sensitivity level is based on previously captured arrhythmic ECG segments. This may include the total number of arrhythmic ECG segments captured, and/or the number of arrhythmic ECG segments captured with respect to the rate-based threshold utilized to capture the most recent ECG segment. For example, if following capture of an ECG segment representing a tachycardia rate above 130 BPM (e.g., tachy130 event), step 203 may review the count of previously captured tachy130 events. If the number of previously captured tachy130 events exceeds a threshold, then the sensitivity/specificity level associated with tachy130 events is adjusted (e.g., decreasing the sensitivity level in order to require that subsequent tachy130 events are detected with greater specificity). Determining whether to adjust the sensitivity level of the sensitivity profile based on the captured ECG segment includes balancing a number of considerations, including, but not limited to, the severity of the arrhythmia and the sensitivity level of the captured ECG segment. For instance, an initially high sensitivity level for an arrhythmia of low severity (e.g., tachy130) can lead to the capture of an excessive number of ECG segments with low clinical relevance as a result of both the significance of the arrhythmia (low) and the risk of false positives (high) due to the high sensitivity level. In this instance, decreasing the sensitivity level decreases the number of false positives detected. In contrast, for more severe arrhythmias it may be desirable to maintain the sensitivity/specificity levels at a determined level despite the number of previously detected events to ensure all events are detected (e.g., no false negatives). Thus, each heart-rate threshold may have an associated sensitivity/specificity profile that indicates how the sensitivity/specificity will change. In one embodiment, heart rate thresholds utilized include $R_i$, $R_j$, ... $R_N$, where N is any positive integer. For a particular heart rate threshold, $R_i$, an initial or first sensitivity level can be represented as $X_i/Y_i$ and subsequently adjusted sensitivity levels can be represented as $X_{i+1}/Y_{i+1}$, $X_{i+2}/Y_{i+2}$, and so on, up to $X_{i+n}/T_{i+n}$, where $X_{i+1}/Y_{i+1}$ refers to the first adjusted sensitivity level, $X_{i+2}/Y_{i+2}$ refers to the second adjusted sensitivity level, and $X_{i+n}/Y_{i+n}$ refers to the nth adjusted sensitivity level, where n is any positive integer. Collectively, $X_i/Y_i \ldots X_{i+n}/Y_{i+n}$ refers to the sensitivity profile associated with the heart rate threshold $R_1$.

In the embodiment described above, previously detected arrhythmic ECG events are utilized to determine whether to adjust the sensitivity/specificity level. However, a number of other factors may be utilized alone or in combination to determine whether to adjust the sensitivity level. These factors include, but are not limited to, a period of elapsed time, patient-specific considerations, and/or a desired clinical relevance of captured arrhythmic episodes. The sensitivity profiles of the present invention can be adjusted based on any number of considerations known to those of skill in the art.

Table 1 provides an example of sensitivity profiles for each of Tachy130, Tachy150, Tachy165, and Tachy180:

TABLE 1

Tachycardia Sensitivity Profiles Associated with Heart Rate Thresholds

| | | Sensitivity Profiles | | |
|---|---|---|---|---|
| ECG Episode | Heart Rate Threshold | Initial Sensitivity Level | 1st Adjusted Sensitivity Level | 2nd Adjusted Sensitivity Level |
| Low Rate Tachycardia (Tachy130) | 130 BPM | 13/20 | 18/20 | 23/25 |
| Mid-Medium Rate Tachycardia (Tachy150) | 150 BPM | 10/20 | 13/20 | 18/25 |
| Mid-High Rate Tachycardia (Tachy165) | 165 BPM | 8/20 | 8/20 | 13/25 |
| High Rate Tachycardia (Tachy180) | 180 BPM | 5/20 | 5/20 | 5/20 |

Table 1 thus shows a plurality of heart rate thresholds (130 BPM, 150 BPM, 165 BPM, and 180 BPM) for detecting tachycardia. Each heart rate threshold includes three sensitivity levels: an initial sensitivity level, a first adjusted sensitivity level, and a second adjusted sensitivity level. For instance, for a 130 BPM heart rate threshold, the initial sensitivity level is 13/20, the first adjusted sensitivity level is 18/20, and the second adjusted sensitivity level is 23/25. Those three sensitivity levels can collectively be referred to as a sensitivity profile for a heart rate threshold of 130 BPM, or tachy130. As shown in Table 1, the sensitivity levels associated with each of the heart rate thresholds increases with the severity of the tachycardia (e.g., from tachy130 to tachy180). This ensures ECG segments associated with severe tachycardia are detected and captured.

Table 2 provides an example of sensitivity profiles for each of Brady30, Brady40, and Brady50:

TABLE 2

Bradycardia Sensitivity Profiles Associated with Heart Rate Thresholds

| | | Sensitivity Profiles | | |
|---|---|---|---|---|
| ECG Episode | Heart Rate Threshold | Initial Sensitivity Level | 1st Adjustment Sensitivity Level | 2st Adjustment Sensitivity Level |
| Low Rate Bradycardia (Brady30) | 30 BPM | 3/4 | 3/4 | 3/4 |
| Medium Rate Bradycardia (Brady40) | 40 BPM | 8/20 | 10/20 | 13/25 |
| High Rate Bradycardia (Brady50) | 50 BPM | 10/20 | 13/20 | 18/25 |

Similarly, Table 2 shows a plurality of heart rate thresholds (30 BPM, 40 BPM, and 50 BPM) for detecting bradycardia. Each heart rate threshold includes three sensitivity levels: an initial sensitivity level, a first adjusted sensitivity level, and a second adjusted sensitivity level. For instance, for a 50 BPM heart rate threshold, the initial sensitivity level is 10/20, the first adjusted sensitivity level is 13/20, and the second adjusted sensitivity level is 18/25. Those three sensitivity levels can collectively be referred to as a sensitivity profile for a heart rate threshold of 50 BPM, or brady50. As shown in Table 1, the sensitivity levels associated with each of the heart rate thresholds increases with the severity of the bradycardia (e.g., from brady50 to brady30). This ensures ECG segments associated with severe bradycardia are detected and captured.

In one embodiment, the sensitivity levels are adjusted according to the defined sensitivity profiles based on a count of previously detected ECG segments, which, as explained above, can be in response to a severity of the arrhythmia and a sensitivity level of the previously or most recently captured ECG segment. In some embodiments, the sensitivity levels of sensitivity profiles are automatically and/or manually adjusted based on preset settings. In some embodiments, the sensitivity levels of sensitivity profiles are automatically and/or manually adjusted remotely, such as from a remote monitoring center. In some embodiments, the sensitivity levels of sensitivity profiles are automatically and/or manually adjusted via direct and/or indirect inputs to the patient-monitoring device.

Steps 205 and 206 are optional. In some embodiments, if at step 203 it is determined that the sensitivity level should not be adjusted, then the method continues at step 201 monitoring the ECG signals of the patient. However, in the embodiment shown in FIG. 2, steps 205 and 206 allow for resetting the sensitivity level to an initial level. For example, this allows the sensitivity level to be reset after a set period of time (e.g., one day, one week) to increase the number of arrhythmic ECG segments captured. In addition, resetting the sensitivity level accounts for changes in patient status. Although in the embodiment shown in FIG. 2, the sensitivity level is reset to an initial sensitivity level, in other embodiments the sensitivity level is reset to a level determined by the sensitivity profile.

Figure 3:
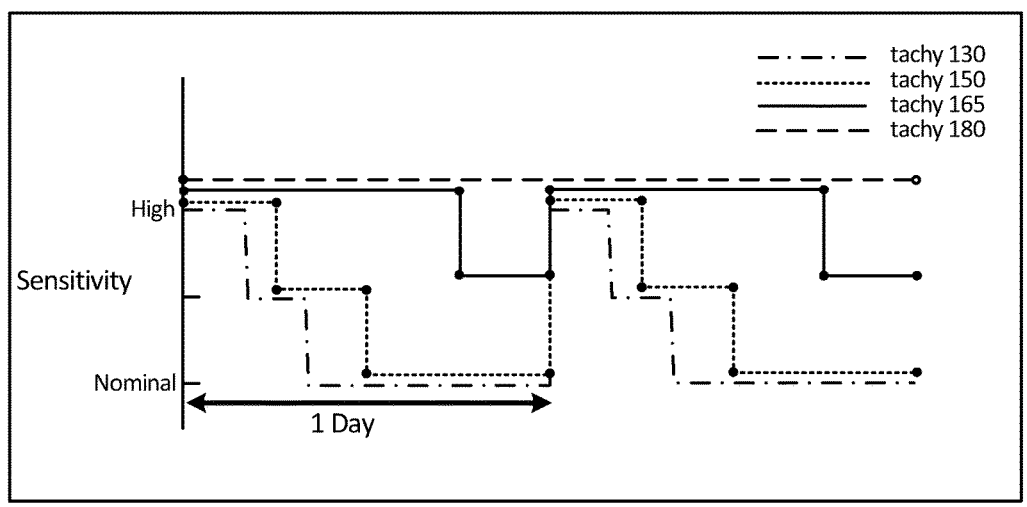
FIG. 3 illustrates a graphical view of adjustments made to sensitivity levels for a plurality of heart rate thresholds (e.g., tachycardia) as a function of previously detected ECG segments, according to one or more embodiments of the present disclosure.

FIG. 3 is a graph that illustrates for a plurality of heart rate thresholds (e.g., tachycardia) adjustments made to the sensitivity levels of each as a function of previously detected arrhythmic ECG segments. As shown in FIG. 3, sensitivity profiles for tachy130, tachy150, tachy165, and tachy180 are shown. Due to the severity of a tachy180 arrhythmia, the sensitivity setting remains constant and at the highest level. This ensures that most or all ECG segments associated with tachy180 events are captured and reported. On the other hand, the sensitivity of the other tachycardia episodes decreases in response to previously detected ECG segments, with the sensitivity settings decreasing at a greater rate for the lower rate tachycardia. For instance, the sensitivity profile for tachy130 decreases more rapidly throughout the course of the day than tachy150. Similarly, the sensitivity settings for tachy150 decreases more rapidly throughout the course of the day than tachy165. Also shown in FIG. 3 is the resetting of sensitivity profiles at the end of each day to their initial levels.

Figure 4:
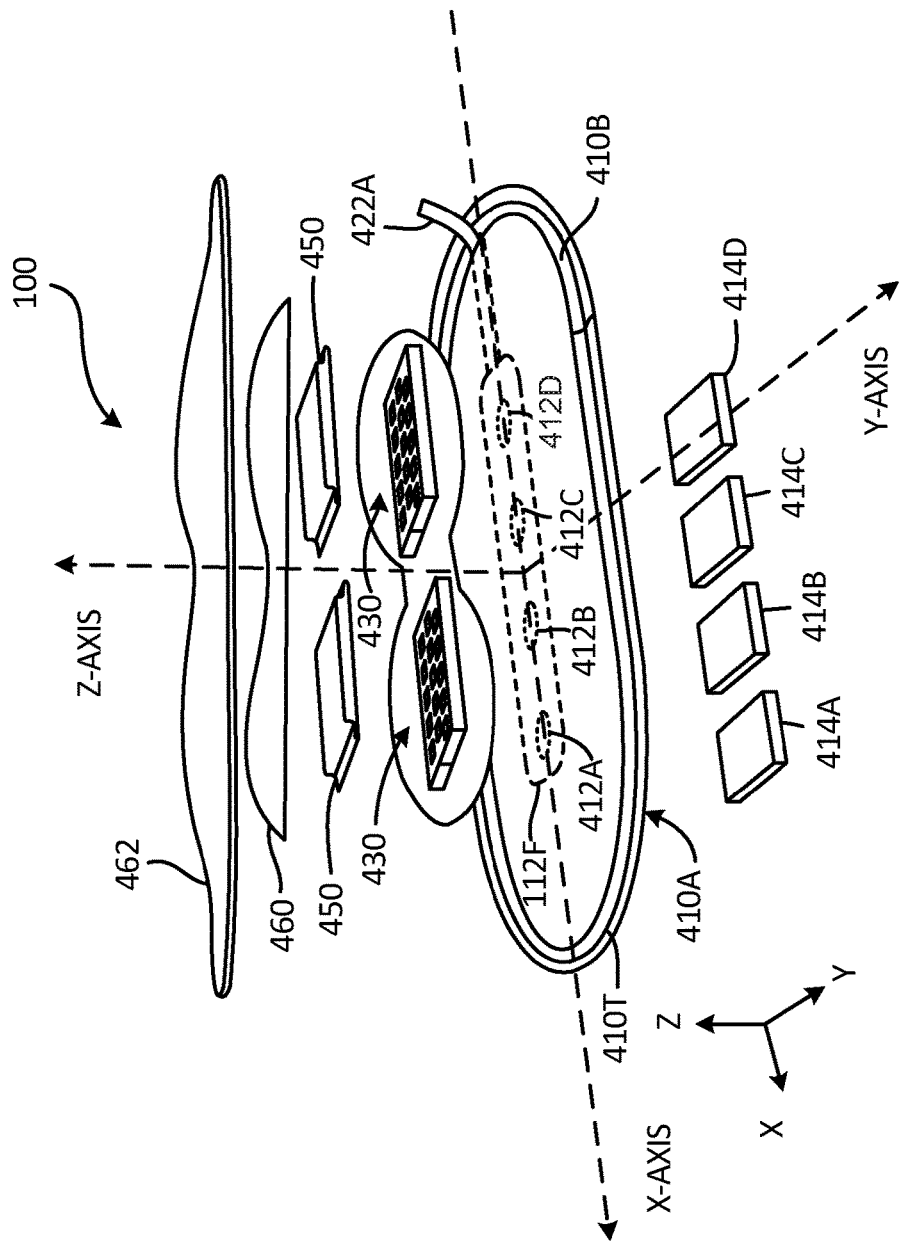
FIG. 4 illustrates a schematic diagram of an adherent device for detecting electrocardiogram signals, according to one or more embodiments of the present invention.

FIG. 4 is an exploded view, respectively, of monitoring device 400 with adaptive arrhythmia detection, according to one or more embodiments of the present disclosure. In the embodiment shown in FIG. 4, monitoring device 400 is an adherent device, but as described above may also be implemented as an implantable device, an injectable device, or similar wearable device. In the embodiment shown in FIG. 4, adherent device 400 includes adherent tape 410T, electrodes 412A, 412B, 412C, 412D with gels 414A, 414B, 414C, 414D, printed circuit board (PCB) 420, flexible connected 422A, electrical components/sensors 430 mounted on PCB 420, batteries 450, electronics housing cover 460, and flexible cover 462.

Adherent device 400 comprises at least two electrodes—although the embodiment shown in FIG. 4 includes electrodes 412A, 412B, 412C and 412D. Adherent device 400 may comprise a maximum dimension, for example a maximum length from about 4 to 10 inches, a maximum thickness along a profile of the device from about 0.2 inches to about 0.6 inches, and a maximum width from about 2 to about 4 inches. The adherent patch 400 comprises a first side, or a lower side 410A, that is oriented toward the skin of the patient when placed on the patient. The adherent patch 400 may also comprise a tape 410T which is a material, preferably breathable, with an adhesive (not shown) to adhere to patient P. Electrodes 412A, 412B, 412C and 412D are affixed to adherent patch 400. In many embodiments, at least four electrodes are attached to the patch. Gels 414A, 414B, 414C and 414D can each be positioned over electrodes 412A, 412B, 412C and 412D, respectively, to provide electrical conductivity between the electrodes and the skin of the patient. Adherent patch 400 also comprises a second side, or upper side 410B. In many embodiments, electrodes 412A, 412B, 412C and 412D extend from lower side 410A through adherent patch 100 to upper side 410B. An adhesive can be applied to upper side 410B to adhere structures, for example a breathable cover, to the patch such that the patch can support the electronics and other structures when the patch is adhered to the patient. In many embodiments, adherent patch 100 may comprise a layer of breathable tape 410T, for example a tricot-knit polyester fabric, to allow moisture vapor and air to circulate to and from the skin of the patient through the tape. Electrical signals received at electrodes 412A-412D may be communicated to electronic components 430 via flexible connection 422A, which is connected to a PCB (not shown). Cover 460 is positioned over batteries 450 and electronic components 430 to provide protection for both. In addition, flexible cover 462 is positioned to encase the flexible PCB 420, electronics components 430, and/or adherent patch 410 so as to protect at least the electronics components and the PCB In addition, electronic components 430 may include ECG circuitry utilized to generate electrocardiogram signals and data from two or more of electrodes 412A, 412B, 412C and 412D in many ways. In some embodiments, ECG circuitry (not shown) is connected to inner electrodes 412B and 412C, which may comprise sense electrodes of the impedance circuitry as described above. In many embodiments, the ECG circuitry may measure the ECG signal from electrodes 412A and 412D when current is not passed through electrodes 412A and 412D. In addition, electronic components 430 may include bioimpedance circuitry connected to two or more of electrodes 412A, 412B, 412C and 412D to allow electronic components 430 to measure a bioimpedance associated with the patient. In addition, electronic components 430 may include an accelerometer configured to measured motion of the patient.

In addition, electronic circuitry 430 may comprise a processor module that can be configured to analyze physiological parameters monitored by adherent device 400 and to control collection and transmission of data from the electrocardiogram circuitry. In one embodiment, the processor module included as part of electronic circuitry 430 comprises a tangible medium, for example read only memory (ROM), electrically erasable programmable read only memory (EEPROM) and/or random access memory (RAM). Tangible medium may, for example, store heart-rate thresholds to be utilized, as well as rate-based sensitivity levels to be utilized in combination with each heart-rate threshold. Processing of monitored physiological parameters such as ECG signals may be distributed between the local processor module included as part of electronic circuitry 430 and remote monitoring system 106 (shown in FIG. 1).

In one embodiment, a processor and/or a processing module include electronic circuitry configured to process monitored ECG signals of a patient, detect rhythm abnormalities (e.g., bradycardia, tachycardia, etc.) for a plurality of threshold heart rates, capture clinically relevant ECG episode based on the rate-based sensitivity levels associated with each of the plurality of threshold heart rates, adjust the sensitivity of at least one of the sensitivity levels, and reset at least one of the sensitivity levels. The processor and/or processing module may also communicate and/or transmit ECG signals and/or captured ECG segments to a remote monitoring center for review by an analysis.

In many embodiments, electronics components 430 comprise wireless communications circuitry (not shown) to communicate with remote center 106. The PCB (not shown) may comprise an antenna to facilitate wireless communication. The antenna may be integral with the PCB or may be separately coupled thereto. The wireless communication circuitry can be coupled to the electrocardiogram circuitry to transmit to a remote center with a communication protocol at least one of the electrocardiogram signal or other features collected by the adherent device 400. In specific embodiments, the wireless communication circuitry is configured to transmit collected physiological parameters to remote center 106 (shown in FIG. 1) either directly or through gateway 102. The communication protocol comprises at least one of Bluetooth, ZigBee, WiFi, WiMAX, IR, amplitude modulation or frequency modulation. In many embodiments, the communications protocol comprises a two-way protocol such that the remote center is capable of issuing commands to control data collection. For example, in one embodiment a HCP may push updated heart-rate thresholds and/or rate-based sensitivity levels to adherent device 400. For example, a HCP may increase the rate-based sensitivity levels associated with one or more heart-rate thresholds in response to few ECG segments being captured. Conversely, in response to a high number of ECG segments being captured, a HCP may decrease the rate-based sensitivity levels associated with one or more heart-rate thresholds.

Figure 5:
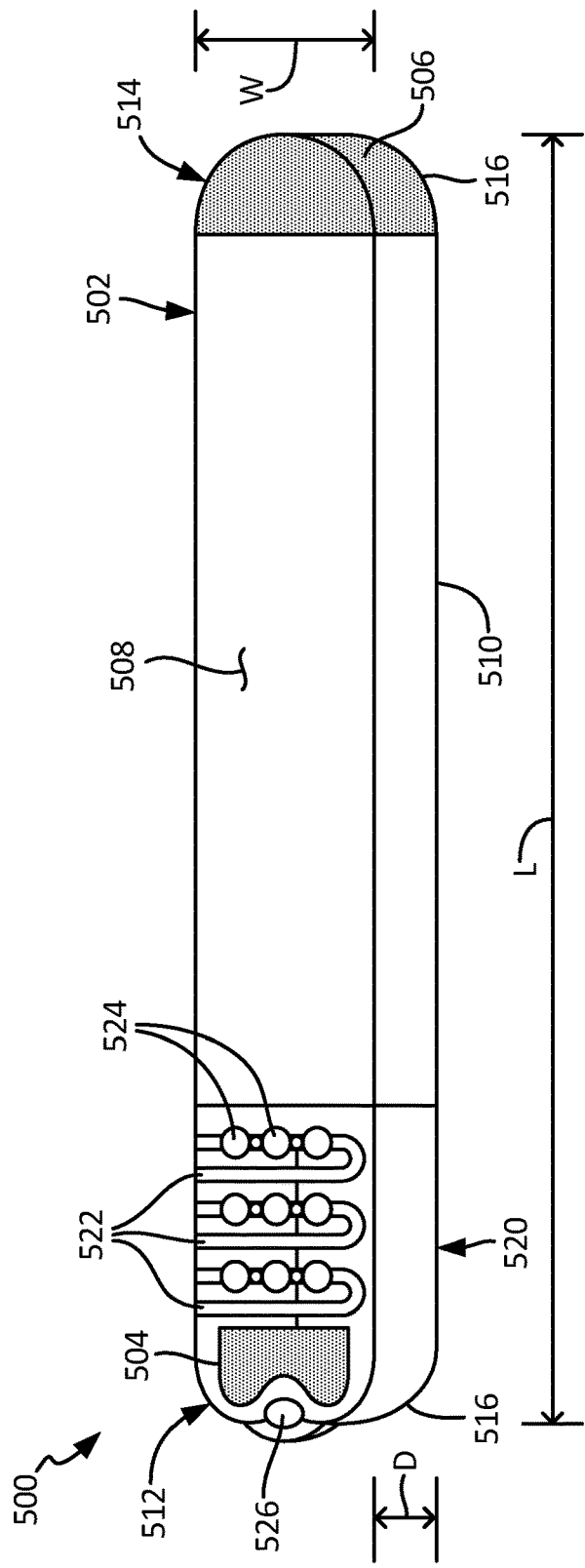
FIG. 5 illustrates a schematic diagram of an insertable cardiac monitor for detecting electrocardiogram signals, according to one or more embodiments of the present disclosure.

FIG. 5 is a perspective view of an insertable monitoring device 500 according to an embodiment of the present invention. In the embodiment shown in FIG. 5, insertable cardiac monitor 500 is defined by a length L, a width W and thickness or depth D and is in the form of an elongated rectangular prism wherein the length L is much larger than the width W, which in turn is larger than the depth D. In one embodiment, the geometry of the insertable cardiac monitor 500—in particular a width W greater than the depth D—is selected to allow the cardiac monitor 500 to be inserted under the skin of the patient using a minimally invasive procedure and to remain in the desired orientation during insert. For example, the device shown in FIG. 5 includes radial asymmetries (notably, the rectangular shape) along the longitudinal axis that maintains the device in the proper orientation following insertion. For example, in one embodiment the spacing between proximal electrode 504 and distal electrode 506 may range from 30 millimeters (mm) to 55 mm, 35 mm to 55 mm, and from 40 mm to 55 mm and may be any range or individual spacing from 25 mm to 60 mm. In addition, insertable cardiac monitor 500 may have a length L that ranges from 30 mm to about 70 mm. In other embodiments, the length L may range from 40 mm to 60 mm, 45 mm to 60 mm and may be any length or range of lengths between about 30 mm and about 70 mm. In addition, the width W of major surface 508 may range from 3 mm to 10 mm and may be any single or range of widths between 3 mm and 10 mm. The thickness of depth D of cardiac monitor device 500 may range from 2 mm to 9 mm. In other embodiments, the depth D of insertable cardiac monitor 500 may range from 2 mm to 5 mm and may be any single or range of depths from 2 mm to 9 mm. In addition, insertable cardiac monitor 500 according to an embodiment of the present invention is has a geometry and size designed for ease of implant and patient comfort. Embodiments of insertable cardiac monitor 500 described in this disclosure may have a volume of three cubic centimeters (cm) or less, 1.5 cubic cm or less or any volume between three and 1.5 cubic centimeters.

In the embodiment shown in FIG. 5, once inserted within the patient, the first major surface 508 faces outward, toward the skin of the patient while the second major surface 510 is located opposite the first major surface 508. In addition, in the embodiment shown in FIG. 5, proximal end 512 and distal end 514 are rounded to reduce discomfort and irritation to surrounding tissue once inserted under the skin of the patient.

As described with other embodiments, proximal electrode 504 and distal electrode 506 are used to sense cardiac signals for determining abnormal cardiac events (e.g., bradycardia, tachycardia, etc.). ECG signals may be stored in a memory of the insertable cardiac monitor 500, and ECG data may be transmitted via integrated antenna 522 to another medical device, which may be another implantable device or an external device, or to a remote monitoring center. In alternative applications, electrodes 504 and 506 may be used for sensing any bio-potential signal of interest, which may be, for example, an EGM, EEG, EMG, or a nerve signal, from any implanted location.

In the embodiment shown in FIG. 5, proximal electrode 504 is in close proximity to the proximal end 512 and distal electrode 506 is in close proximity to distal end 514. In this embodiment, distal electrode 506 is not limited to a flattened, outward facing surface, but may extend from first major surface 508 around rounded edges 516 and onto the second major surface 510 so that the electrode 506 has a three-dimensional curved configuration. In the embodiment shown in FIG. 5, proximal electrode 504 is located on first major surface 508 and is substantially flat, outward facing. However, in other embodiments proximal electrode 504 may utilize the three dimensional curved configuration of distal electrode 506, providing a three dimensional proximal electrode (not shown in this embodiment). Similarly, in other embodiments distal electrode 506 may utilize a substantially flat, outward facing electrode located on first major surface 508 similar to that shown with respect to proximal electrode 504. The various electrode configurations allow for configurations in which proximal electrode 504 and distal electrode 506 are located on both first major surface 508 and second major surface 510. In other configurations, such as that shown in FIG. 5, only one of proximal electrode 504 and distal electrode 506 is located on both major surfaces 508 and 510, and in still other configurations both proximal electrode 504 and distal electrode 506 are located on one of the first major surface 508 or the second major surface 510 (i.e., proximal electrode 504 located on first major surface 508 while distal electrode 506 is located on second major surface 510). In another embodiment, insertable monitoring device 500 may include electrodes on both major surface 508 and 510 at or near the proximal and distal ends of the device, such that a total of four electrodes are included on insertable monitoring device 500. Electrodes 504 and 506 may be formed of a plurality of different types of biocompatible conductive material, e.g. stainless steel, titanium, platinum, iridium, or alloys thereof, and may utilize one or more coatings such as titanium nitride or fractal titanium nitride.

In the embodiment shown in FIG. 5, proximal end 512 includes a header assembly 520 that includes one or more of proximal electrode 504, integrated antenna 522, anti-migration projections 524, and/or suture hole 526. Integrated antenna 522 is located on the same major surface (i.e., first major surface 508) as proximal electrode 504 and is also included as part of header assembly 520. Integrated antenna 522 allows insertable monitoring device 500 to transmit and/or receive data. In other embodiments, integrated antenna 522 may be formed on the opposite major surface as proximal electrode 504, or may be incorporated within the housing 522 of insertable monitoring device 500. In one embodiment, electronic circuitry (not shown) may be housed within housing 522. As described above with respect to FIG. 4, electronic circuitry may include a tangible medium for storing the plurality of heart-rate thresholds and rate-based sensitivity levels. In addition, electronic circuitry may include sensing circuitry for sensing one or more physiological parameters, such as ECG signals, accelerometer signals, and/or bio-impedance signals, and may include a processor module for processing monitored ECG signals to detect arrhythmic ECG segments based on the heart-rate thresholds and rate-based sensitivity levels.

In the embodiment shown in FIG. 5, anti-migration projections 524 are located adjacent to integrated antenna 522 and protrude away from first major surface 508 to prevent longitudinal movement of the device. In the embodiment shown in FIG. 5, anti-migration projections 524 includes a plurality (e.g., nine) small bumps or protrusions extending away from first major surface 508. As discussed above, in other embodiments anti-migration projections 524 may be located on the opposite major surface as proximal electrode 504 and/or integrated antenna 522. In addition, in the embodiment shown in FIG. 5 header assembly 520 includes suture hole 526, which provides another means of securing insertable monitoring device 500 to the patient to prevent movement following insert. In the embodiment shown, suture hole 526 is located adjacent to proximal electrode 504. In one embodiment, header assembly 520 is a molded header assembly made from a polymeric or plastic material, which may be integrated or separable from the main portion of insertable monitoring device 500.

Discussion of Possible Embodiments

The following are non-exclusive descriptions of possible embodiments of the present invention.

A method of adaptive arrhythmia detection. The method may include monitoring ECG signals of a patient via a patient medical device. In addition, the method may include detecting and capturing ECG segments based on a heart rate threshold and an initial sensitivity level associated with the heart rate threshold. Based on previously captured ECG segments, the method may include adjusting the sensitivity level.

The method of the preceding paragraph can optionally include, additionally and/or alternatively any, one or more of the following features, configurations and/or additional components.

The method may further include wherein monitoring ECG signals of a patient via a medical device includes sensing ECG signals. In addition, the method may further include wherein the patient medical device is one or more of an adherent device, an implantable device, an insertable device, and a wearable device.

The method may further include wherein the detecting and capturing ECG segments based on a heart rate threshold and an initial sensitivity level associated with the heart rate threshold includes determining the number of beats above the heart rate threshold in a case of tachycardia and below the heart rate threshold in a case of bradycardia. In addition, the method may further include wherein the detecting and capturing ECG segments based on a heart rate threshold and an initial sensitivity level associated with the heart rate threshold includes one or more of storing an ECG segment to memory and communicating an ECG segment for one or more of in-monitoring analysis and post-monitoring analysis.

The method may further include wherein the adjusting the sensitivity level based on a previously captured ECG segment includes one or more of increasing the sensitivity level and decreasing the sensitivity level. In addition, the method may further include wherein the adjusting the sensitivity level based on a previously captured ECG segment includes modifying one or more of a X parameter and a Y parameter, the X parameter including the number of detected heart beats above the heart rate threshold in the case of tachycardia and below the heart rate threshold in the case of bradycardia, and the Y parameter including the total number of detected heart beats.

The method may further include resetting the sensitivity level periodically.

In another embodiment, a method of adaptive arrhythmia detection. The method may include monitoring ECG signals of a patient via a patient medical device. In addition, the method may include detecting and capturing ECG segments based on a plurality of heart rate thresholds and one or more sensitivity levels associated with each of the heart rate thresholds. The method may further include adjusting at least one or more sensitivity levels associated with each of the heart rate thresholds.

The method of the preceding paragraph can optionally include, additionally and/or alternatively any, one or more of the following features, configurations and/or additional components.

The method may further include wherein the monitoring ECG signals of a patient via a patient medical device includes sensing ECG signals. In addition, the method may further include wherein the patient medical device is one or more of an adherent device, an implantable device, an insertable device, and a wearable device.

The method may further include wherein the detecting and capturing ECG segments based on a plurality of heart rate thresholds and one or more sensitivity levels associated with each of the heart rate thresholds includes determining the number of beats above the heart rate threshold in a case of tachycardia and below the heart rate threshold in a case of bradycardia. In addition, the method may further include wherein the detecting and capturing ECG segments based on a plurality of heart rate thresholds and one or more sensitivity levels associated with each of the heart rate thresholds includes one or more of storing an ECG segment to memory and communicating an ECG segment for one or more of in-monitoring analysis and post-monitoring analysis.

The method may further include wherein the adjusting at least one of the one or more sensitivity levels associated with each of the heart rate thresholds includes one or more of increasing the sensitivity level and decreasing the sensitivity level. In addition, the method may further include wherein the adjusting at least one of the one or more sensitivity levels associated with each of the heart rate thresholds includes adjusting the sensitivity level based on one or more of a previously detected ECG segment, a period of elapsed time, a desired clinical relevance of captured ECG segments, and patient-specific considerations.

The method may further include resetting at least one of the one or more sensitivity levels periodically.

In another embodiment, a medical device may include one or more electrodes, sensing circuitry, and a processing module. The one or more electrodes and sensing circuitry may monitor ECG signals of a patient. The processing module may be configured to receive the monitored ECG signal. In addition, the processing module may be configured to detect and capture ECG segments based on a plurality of heart rate thresholds and one or more sensitivity levels associated with each of the heart rate thresholds. In addition, the processing module may be configured to adjust at least one of the one or more sensitivity levels associated with each of the heart rate thresholds.

The medical device of the preceding paragraph can optionally include, additionally and/or alternatively any, one or more of the following features, configurations and/or additional components.

The medical device may further include wherein the patient medical device is one or more of an adherent device, an implantable device, an insertable device, and a wearable device.

The medical device may further include wherein the processing module is further configured to communicate the captured ECG segment to a patient and/or a remote monitoring center for one or more of in-monitoring review and post-monitoring review. In addition, the medical device may further include wherein the processing module is further configured to reset at least one of the one or more sensitivity levels periodically.

Other embodiments of the present disclosure are possible. Although the description above contains much specificity, these should not be construed as limiting the scope of the disclosure, but as merely providing illustrations of some of the presently preferred embodiments of this disclosure. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form various embodiments. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

The foregoing description of various preferred embodiments of the disclosure have been presented for purposes of illustration and description. It is not intended to be exhaustive or to limit the disclosure to the precise embodiments, and obviously many modifications and variations are possible in light of the above teaching. The example embodiments, as described above, were chosen and described in order to best explain the principles of the disclosure and its practical application to thereby enable others skilled in the art to best utilize the disclosure in various embodiments and with various modifications as are suited to the particular use contemplated. It is intended that the scope of the disclosure be defined by the claims appended hereto Various examples have been described. These and other examples are within the scope of the following claims.

What is claimed is:

1. A method of adaptive arrhythmia detection, the method comprising:
   monitoring ECG signals of a patient via a patient medical device;
   detecting arrhythmic ECG segments based on a heart rate threshold and an initial sensitivity level associated with the heart rate threshold;
   incrementing a count of detected arrhythmic ECG segments in response to each arrhythmic ECG segment detected; and
   increasing the sensitivity level associated with the heart rate threshold in response to the count of detected arrhythmic ECG segments failing to exceed a threshold within a given time period.

2. The method of claim 1, wherein monitoring ECG signals of a patient via a patient medical device includes sensing ECG signals.

3. The method of claim 1, wherein the patient medical device is one or more of an adherent device, an implantable device, an insertable device, and a wearable device.

4. The method of claim 1, wherein detecting arrhythmic ECG segments based on a heart rate threshold and an initial sensitivity level associated with the heart rate threshold includes determining the number of beats above the heart rate threshold in a case of tachycardia and below the heart rate threshold in a case of bradycardia.

5. The method of claim 1, wherein detecting arrhythmic ECG segments based on a heart rate threshold and an initial sensitivity level associated with the heart rate threshold includes one or more of storing the arrhythmic ECG segment to memory and communicating the arrhythmic ECG segment for one or more of in-monitoring analysis and post-monitoring analysis.

6. The method of claim 1, wherein the adjusting the sensitivity level based on a previously detected arrhythmic ECG segment includes modifying one or more of a X parameter and a Y parameter, the X parameter including the number of detected heart beats above the heart rate threshold in the case of tachycardia and below the heart rate threshold in the case of bradycardia, and the Y parameter including the total number of detected heart beats.

7. The method of claim 1, further comprising resetting the sensitivity level periodically.

8. The method of claim 7, wherein resetting the sensitivity level includes resetting the sensitivity level to the initial sensitivity level.

9. The method of claim 7, wherein resetting the sensitivity level includes resetting the sensitivity level to a sensitivity level determined by a sensitivity profile.

10. The method of claim 1, wherein increasing the sensitivity level further includes increasing the sensitivity level based on one or more of a period of elapsed time, a desired clinical relevance of captured ECG segments, and patient-specific considerations.

11. The method of claim 1, wherein the heart rate threshold includes a plurality of heart rate thresholds corresponding to arrhythmias of various severity, each heart rate threshold characterized by a sensitivity profile, wherein the sensitivity associated with one or more of the plurality of heart rate thresholds is increased in response to the count of detected arrhythmic ECG segments associated with one or more of the heart rate thresholds failing to exceed a threshold within a given time period.

12. The method of claim 1, further including:
   decreasing the sensitivity level associated with the heart rate threshold in response to the count of detected arrhythmic ECG segments exceeding a threshold.

13. The method of claim 12, wherein the heart rate threshold includes a plurality of heart rate thresholds corresponding to arrhythmias of various severity, each heart rate threshold characterized by a sensitivity profile, wherein the sensitivity associated with one or more of the plurality of heart rate thresholds is decreased in response to the count of detected arrhythmic ECG segments associated with one or more of the heart rate thresholds exceeding a threshold.

14. A patient medical device, the device comprising:
   one or more electrodes and sensing circuitry for monitoring ECG signals of a patient; and
   a processing module configured to receive the monitored ECG signal, wherein the processing module detects and captures ECG segments based on a plurality of heart rate thresholds and one or more sensitivity levels associated with each of the heart rate thresholds, increments a count of detected arrhythmic ECG segments corresponding to one of the heart rate thresholds in response to each arrhythmic ECG segment detected based on the heart rate threshold and associated sensitivity level, and increases the sensitivity level associated with the heart rate threshold having a corresponding count of detected arrhythmic ECG segments that fails to exceeds a threshold within a given time period.

15. The patient medical device of claim 14, wherein the patient medical device is one or more of an adherent device, an implantable device, an insertable device, and a wearable device.

16. The patient medical device of claim 14, wherein the processing module is further configured to communicate the captured arrhythmic ECG segment to a patient and/or a remote monitoring center for one or more of in-monitoring review and post-monitoring review.

17. The patient medical device of claim 14, wherein the processing module is further configured to reset at least one of the one or more sensitivity levels periodically.

18. The patient medical device of claim 14, wherein the processing module is further configured to increase the sensitivity level based on one or more of a period of elapsed time, a desired clinical relevance of captured ECG segments, and patient-specific considerations.

19. The patient medical device of claim 18, wherein the processing module is further configured to decrease the sensitivity level associated with the heart rate threshold in response to the count of detected arrhythmic ECG segments exceeding a threshold.

* * * * *